US010171029B2

(12) United States Patent
Gostein et al.

(10) Patent No.: US 10,171,029 B2
(45) Date of Patent: Jan. 1, 2019

(54) SOILING MEASUREMENT DEVICE FOR PHOTOVOLTAIC ARRAYS EMPLOYING MICROSCOPIC IMAGING

(71) Applicants: Michael Gostein, Austin, TX (US); William Stueve, Austin, TX (US)

(72) Inventors: Michael Gostein, Austin, TX (US); William Stueve, Austin, TX (US)

(*) Notice: Subject to any disclaimer, the term of this patent is extended or adjusted under 35 U.S.C. 154(b) by 0 days.

(21) Appl. No.: 15/877,351

(22) Filed: Jan. 22, 2018

(65) Prior Publication Data
US 2018/0331654 A1 Nov. 15, 2018

Related U.S. Application Data

(60) Provisional application No. 62/510,347, filed on May 24, 2017, provisional application No. 62/505,343, filed on May 12, 2017.

(51) Int. Cl.
*H02S 50/15* (2014.01)
*G01N 21/94* (2006.01)
*H02S 40/10* (2014.01)

(52) U.S. Cl.
CPC .............. *H02S 50/15* (2014.12); *G01N 21/94* (2013.01); *H02S 40/10* (2014.12)

(58) Field of Classification Search
CPC .......... H02S 50/15; H02S 40/10; G01N 21/94
USPC ........................................................ 356/218
See application file for complete search history.

(56) References Cited

U.S. PATENT DOCUMENTS

| 7,538,800 | B1* | 5/2009 | Caretti | G01M 11/0264 348/180 |
| 8,945,954 | B2* | 2/2015 | Fukazawa | G01N 21/9501 257/E21.527 |
| 9,164,042 | B2* | 10/2015 | Aiko | G01B 11/303 |
| 2008/0088702 | A1* | 4/2008 | Linsenmaier | G03B 17/18 348/119 |
| 2009/0241994 | A1 | 10/2009 | Lee | |
| 2014/0232869 | A1 | 8/2014 | May et al. | |
| 2014/0246611 | A1* | 9/2014 | Sacquard | G01N 21/15 250/559.1 |
| 2016/0104084 | A1 | 4/2016 | Philip et al. | |
| 2017/0194897 | A1* | 7/2017 | Lopez | H02S 40/10 |

FOREIGN PATENT DOCUMENTS

JP 2007110038 4/2007
JP 2014082272 8/2014

* cited by examiner

*Primary Examiner* — Hina F Ayub

(57) ABSTRACT

A device comprising a transparent window, an imaging unit, and a computing element coupled to said imaging unit, wherein said device is configured to allow soiling particles to accumulate on a surface of said transparent window, said imaging unit is configured to capture an image of said surface, and said computing element is configured to perform analysis of said image to determine a soiling level of said transparent window. Additionally, a method of performing said analysis.

18 Claims, 15 Drawing Sheets

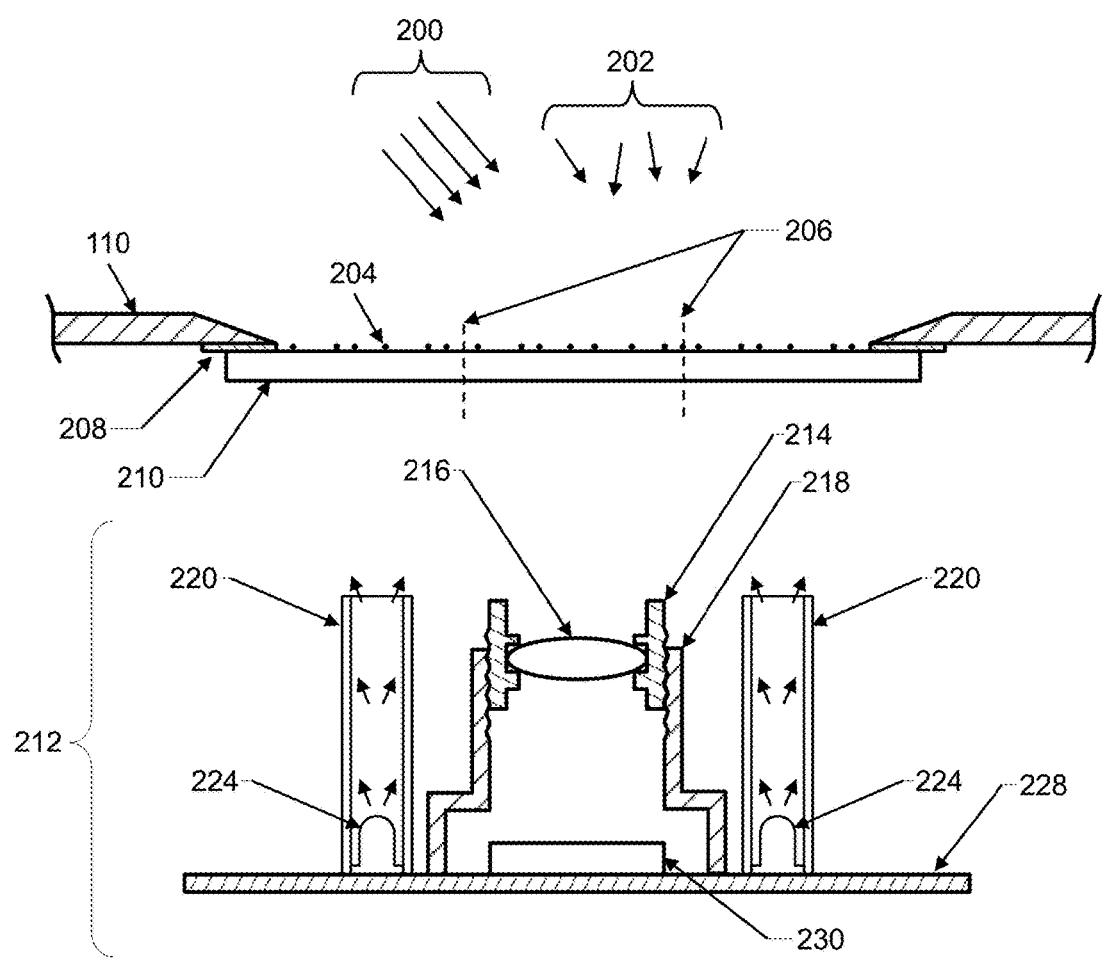

SOILING MEASUREMENT DEVICE FOR PHOTOVOLTAIC ARRAYS EMPLOYING MICROSCOPIC IMAGING

CROSS-REFERENCE TO RELATED APPLICATIONS

This application claims the benefit of U.S. Provisional Patent Application No. 62/510,347, filed on May 24, 2017, entitled "Soiling Measurement Device for Photovoltaic Arrays Employing Microscopic Imaging" and naming Gostein and Stueve as inventors. The above-referenced provisional patent application is hereby incorporated by reference herein in its entirety.

This application claims the benefit of U.S. Provisional Patent Application No. 62/505,343, filed on May 12, 2017, entitled "Optical Soiling Measurement Device for Photovoltaic Arrays" and naming Gostein and Stueve as inventors. The above-referenced patent application is hereby incorporated by reference herein in its entirety.

The subject matter of the present application is related to the subject matter of the commonly assigned, co-pending U.S. patent application Ser. No. 15/877,207, filed on Jan. 22, 2018, the same day as the present application, entitled "Optical Soiling Measurement Device for Photovoltaic Arrays" and naming Gostein and Stueve as inventors. The above-referenced patent application is hereby incorporated by reference herein in its entirety.

FIELD OF THE INVENTION

The disclosed subject matter is directed to the measurement of soiling levels of photovoltaic (PV) arrays.

SUMMARY

In one respect, disclosed is a device comprising a transparent window, an imaging unit, and a computing element coupled to said imaging unit, wherein said device is configured to allow soiling particles to accumulate on a surface of said transparent window, said imaging unit is configured to capture an image of said surface, and said computing element is configured to perform analysis of said image to determine a soiling level of said transparent window.

In another respect, disclosed is a method for performing said analysis.

BRIEF DESCRIPTION OF THE DRAWINGS

FIG. 3 depicts a cross-sectional view of an embodiment of a soiling sensor, wherein soiling particles accumulate on the exterior surface of a transparent window which is imaged by an imaging unit.

DETAILED DESCRIPTION OF THE INVENTION

Figure 1:
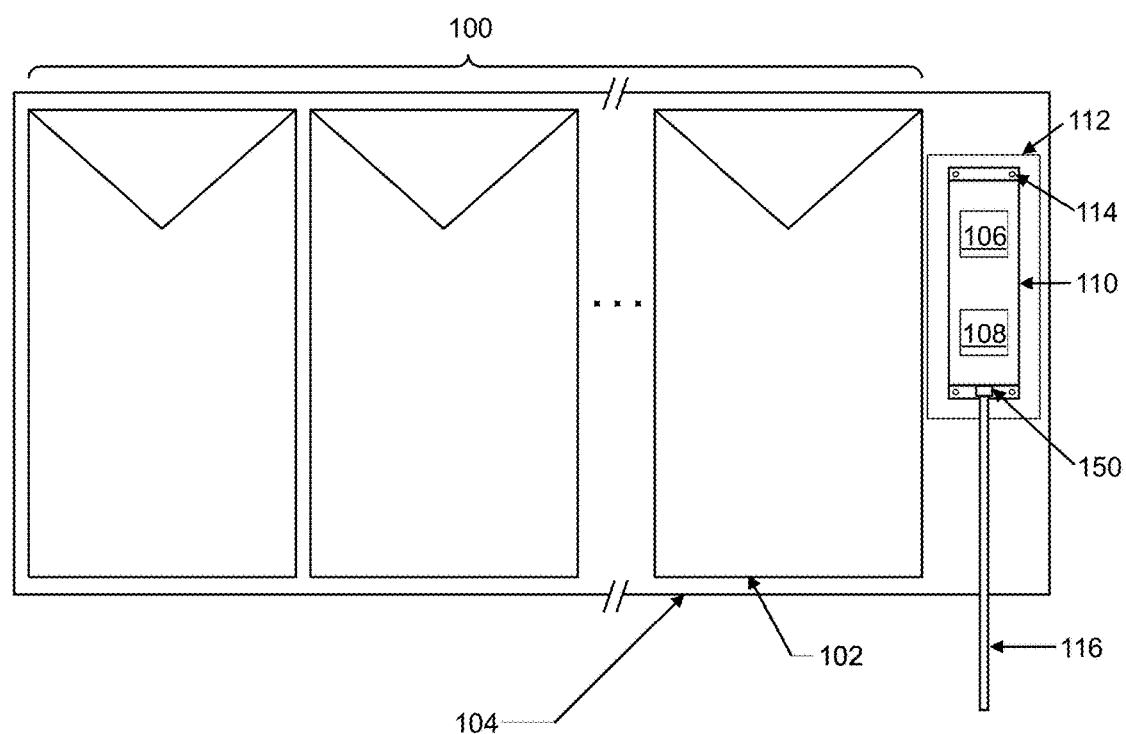
FIG. 1 depicts an embodiment comprising a soiling sensor and irradiance sensor within an enclosure mounted at the site of a PV array.

Solar panels, also known as photovoltaic (PV) modules, are used to convert sunlight to electric power in installations known as PV arrays. An important loss factor for a PV array is the accumulated deposition of airborne particulate matter on the light-receiving surfaces of the PV modules. This accumulation, known as soiling, reduces the power output of a PV array by blocking the transmission of sunlight to the PV cells of the PV array. Soiling particles consist of any airborne particulate matter, such as dust, dirt, soot, pollen, etc., which deposits on a PV array, and have typical diameters ranging from ~0.2 microns to ~200 microns. In dusty outdoor regions without frequent rainfall, the power loss due to soiling, known as soiling loss, can be significant.

In commercial electric power generation applications, which range from small ground-mounted and roof-mounted PV arrays to large utility-scale projects, owners and operators of PV arrays often wish to measure losses due to soiling. Motivations include, but are not limited to, pre-construction assessment of soiling loss as an aid to site selection and performance estimation, validation and monitoring of the performance of an operating PV array, and determination of when to wash a PV array in order to yield greatest return on investment for the expense of washing.

The soiling level, also called soiling loss or transmission loss, is the loss due to soiling particles in the usable light received by the PV cells of the PV array, relative to a clean state. In some embodiments, the soiling level may be defined as the fractional loss in the usable light received, relative to a clean state. Usable light means light that is absorbed by the PV array and is converted, or could be converted, to electrical output. Equivalently, the soiling level can be defined as one minus the fractional transmission of usable light through the layer of soiling particles, relative to a clean state. In the absence of soiling particles the transmission so defined, in some embodiments, is 100% and soiling level is 0%, i.e. transmission is defined relative to the clean state of the device ignoring any other losses not due to soiling. The soiling ratio is defined as the ratio of the PV array electrical output to its expected output in a clean state, or, equivalently, as the fractional transmission of usable light. The measurement of any of soiling level, soiling loss, transmission loss, transmission, or soiling ratio is equivalent, as each is an expression of the loss due to soiling. It should be noted that soiling level, soiling loss, transmission loss, transmission, or soiling ratio may also be defined using alternative mathematical functions and/or scales, where such scales include for example fractional values, percentages, logarithmic scales, units of power, and units of energy, and that each of these alternative terms, mathematical functions, and/or scales is intended to be within the scope of this disclosure.

In some embodiments, a device is disclosed that is configured to measure a soiling level characteristic of a PV array or prospective PV array.

In some embodiments, a soiling level measurement device is disclosed that does not require routine cleaning of a reference device to perform its measurement.

In some embodiments, soiling level is determined by analysis of microscopic images of deposited soiling particles. Some embodiments may have any of the following aspects: microscopic images may be acquired using sunlight without the use of an external artificial light source; the precision of said analysis is decoupled from or compensates for normal variations in intensity of sunlight or internal illumination sources; said microscopic images capture the effects of soiling particles smaller than the resolution of said microscopic images; the field of view of said microscopic images is maximized, based on a resolution of said microscopic images and a size distribution and area coverage of soiling particles.

In some embodiments, a device according to the disclosed subject matter may be installed in close proximity to a PV array or at the site of prospective PV array. The soiling level detected on the device itself may be assumed to be characteristic of the soiling level on the PV array or prospective PV array. Since the accumulation of soiling particles can depend on orientation, especially tilt angle, the device may be typically installed in the same plane (same azimuth and tilt angle) as an actual or prospective PV array. In some embodiments, the device mounts onto a PV array mounting structure or onto a PV module within a PV array, especially in embodiments where a PV array is a tracking system that moves throughout the day to track the sun.

FIG. 1 depicts a device in accordance with some embodiments mounted within a photovoltaic array (100). A soiling sensor (108) and an optional irradiance sensor (106) are incorporated within a weather-resistant sealed enclosure (110). The enclosure (110) may be mounted via mounting holes (114) to a mounting bracket (112) which in turn may be mounted to a PV array mounting structure (104) in close proximity to a PV module (102) of PV array (100). Power and communication cabling (116) may pass through a cable feedthrough (150) and carry electrical power and communication signals from the device to another location from which the device is powered and to which data are reported. Enclosure (110) may be mounted such that soiling sensor (108) and optional irradiance sensor (106) are co-planar (or in a parallel plane) to PV module (102) and PV array (100).

Figure 2A:
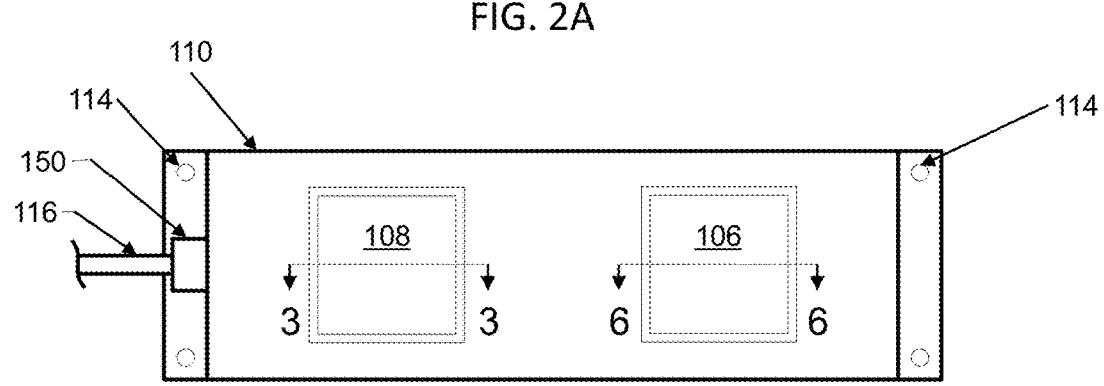
FIG. 2A depicts a top view of an embodiment comprising a soiling sensor and irradiance sensor within an enclosure.
Figure 2B:
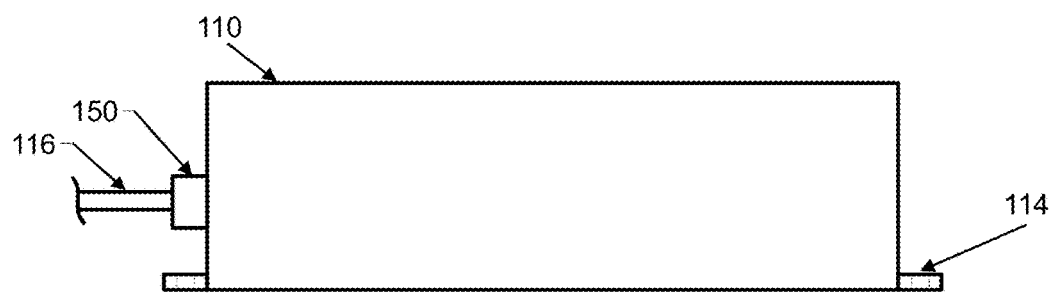
FIG. 2B depicts a side exterior view of an embodiment depicted in FIG. 2A.

FIG. 2A and FIG. 2B, respectively, depict top and side views in accordance with some embodiments similar to those depicted in FIG. 1.

In some embodiments, power and communication cabling (116) may consist of multiple cables entering at multiple cable feedthroughs (150). In some embodiments, the device is self-powered, for example via an onboard solar panel, and/or data communication is performed wirelessly, such that power and communication cabling (116) are omitted.

In some embodiments, the device includes multiple soiling sensors (108) and/or multiple irradiance sensors (106).

FIG. 3 depicts a cross-sectional view of soiling sensor (108) in accordance with some embodiments. A transparent window (210), fabricated for example from glass or plastic, is bonded within a cutout or hole in enclosure (110) with a seal material (208), such that soiling particles (204) can collect on transparent window (210) in the same manner as soiling particles (204) would collect on PV array (100). Soiling particles (204) may be illuminated by direct sunlight (200) and/or diffuse sunlight (202), or, in some embodiments, by internal illumination sources (224) which direct light via optional diffusers or light guides (220) to the underside of transparent window (210). An imaging unit (212) acquires an image of an object plane, comprising the exterior surface of transparent window (210) with accumulated soiling particles (204), within a field of view (206). Imaging unit (212) may comprise imaging optics (216) which project an image of the object plane onto an image sensor (230) mounted, for example, on a printed circuit board (228). Imaging optics (216) may be held within an optics housing (214) which itself may be held within an optics mount (218). Soiling level may be determined from analysis of images collected from image sensor (230), as will be described below. Exemplary image sensors (230) may capture images using, for example, a 2592×1944 pixel array.

In some embodiments, field of view (206) may be maximized while remaining small enough that at least a portion of the clear spaces between soiling particles (204) remains larger than the resolution of said image, although soiling particles (204) themselves may be smaller than said resolution, as described below.

In some embodiments, image analysis comprises determining reference brightness values (or pixel brightness values) corresponding to substantially lossless light transmission (for example, in clear areas in between soiling particles (204)) and substantially complete attenuation of relative light transmission (for example, in areas where light is blocked by soiling particles (204)), assigning light transmission values (or relative brightness values) to pixels between said limits, and calculating the average light transmission (or average relative brightness) of said pixels. Here relative light transmission means transmission through transparent window (210) relative to a clean state of said transparent window, neglecting losses other than from soiling particles (204), and relative brightness means brightness relative to a reference brightness corresponding to substantially lossless transmission; substantially lossless means relative transmission near 100%, within a degree of tolerance chosen as a specification of the device, for example 1%, 2%, or 5%; substantially complete attenuation means relative transmission near 0%, within said degree of tolerance. In contrast to a method that depends on a stable illumination intensity as a reference to determine transmission loss by measuring attenuation of signal received from a light source, such as an external or internal artificial light source, said analysis is substantially insensitive to variations in illumination intensity, such as variations in sunlight (200, 202) or illumination sources (224), because in some embodiments reference brightness values are determined from said image, as described below, and therefore compensate for variations in illumination intensity.

In some embodiments, imaging optics (216) may be a single simple lens or a multi-element compound lens mounted within optics housing (214), and optics housing (214) may mount within optics mount (218) for example by threading as depicted in FIG. 3.

Although imaging optics (216) are depicted in FIG. 3 as a single lens, in various embodiments imaging optics (216) could include multiple optical elements and assemblies and could include lenses, mirrors, and filters.

As depicted in FIG. 3, optics mount (218) may also serve the purpose of blocking light from reaching image sensor (230) except via imaging optics (216).

Imaging unit (212) may be held at a defined position from the object plane comprising the exterior surface of transparent window (210), wherein the defined position is either fixed or may be adjusted during assembly or maintenance of the device in order to bring the object plane into focus at image sensor (230). Focus may also be achieved by adjusting the position of imaging optics (216). For example, in some embodiments, focus may be achieved during assembly or maintenance of the device by rotating threaded optics housing (214) within threaded optics mount (218), after which the position of optics housing (214) is locked with a lock ring or lock screw.

In some embodiments, imaging optics (216) and the distance between image sensor (230) and the exterior surface of transparent window (210) are chosen so as to maximize field of view (206) while maintaining sufficient resolution to detect clear areas in between soiling particles (204), as explained below.

In some embodiments, transparent window (210) comprises or is supplemented by a filter that reduces the intensity of incident direct sunlight (200) and/or diffuse sunlight (202) or alters its spectral composition. In some embodiments transparent window (210) further comprises an anti-reflective coating. In some embodiments, transparent window (210) is bonded to the inside of enclosure (110), as depicted in FIG. 3, while in other embodiments it is bonded to the outside of enclosure (110), to avoid traps for the collection of soiling particles (204).

Direct sunlight (200) comprises collimated light emanating from the sun and directly striking transparent window (210), while diffuse sunlight (202) comprises uncollimated sunlight that is scattered by the atmosphere, clouds, or terrestrial objects prior to striking transparent window (210).

When illuminated by direct sunlight (200) or diffuse sunlight (202), soiling particles (204) block incident light and accordingly the image acquired at image sensor (230) may consist of a light background with shadows corresponding to soiling particles (204) which are backlit, except under certain conditions to be described.

However, in some embodiments, soiling particles (204) on transparent window (210) are illuminated from underneath by light generated inside sealed enclosure (110), for example at night. When transparent window (210) is illuminated from underneath, the image acquired at image sensor (230) may consist of bright pixels corresponding to reflection from soiling particles (204) and dark pixels corresponding to clear spaces between soiling particles (204). In some embodiments, light is generated by internal illumination sources (224) and directed to the underside of transparent window (210) by optional light guides (220), which may also serve as diffuser elements. Illumination sources (224) may comprise, for example, LEDs mounted on printed circuit board (228). In alternative embodiments illumination sources (224) are mounted on a ring or disk, either surrounding optics mount (218) or at a position closer to or directly underneath transparent window (210), with an appropriately-sized hole for imaging, and/or optional light guides (220) are replaced by another light guiding or diffuser element, such as a plastic disk or ring, or are omitted. In some embodiments a diffuser element is designed to prevent the direct imaging of a reflection of illumination sources (224) from transparent window (210), which would complicate image analysis.

Figure 4:
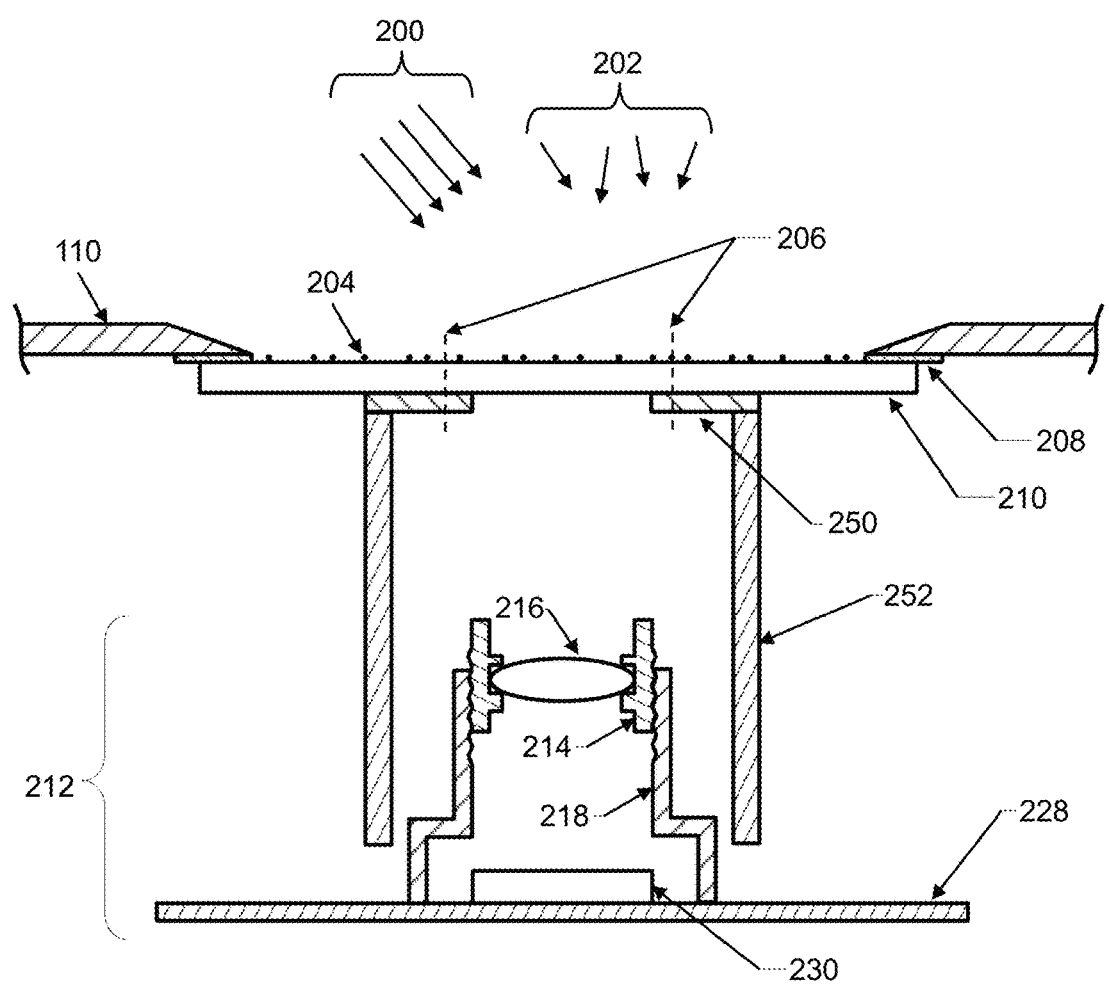
FIG. 4 depicts a cross-sectional view of another embodiment of a soiling sensor, further comprising an aperture and/or shroud.

FIG. 4 depicts alternative elements of soiling sensor (108), in accordance with some embodiments.

In some embodiments, a shroud (252) blocks light which would otherwise enter through transparent window (210) and scatter from interior surfaces of the device into the imaging optics (216).

In some embodiments, an aperture (250) placed in close proximity to transparent window (210) may block part of field of view (206), in order to provide a reference within images acquired at image sensor (230) for pixel brightness values corresponding to shadows, such as projected by soiling particles (204). In some embodiments, aperture (250) may consist of a thin sheet with a window cutout. In some embodiments, aperture (250) may consist of a wire or protrusion that obscures part of field of view (206). In other embodiments, aperture (250) may consist of a small dot painted, etched, or otherwise applied to the interior surface of transparent window (210) within field of view (206).

Figure 5:
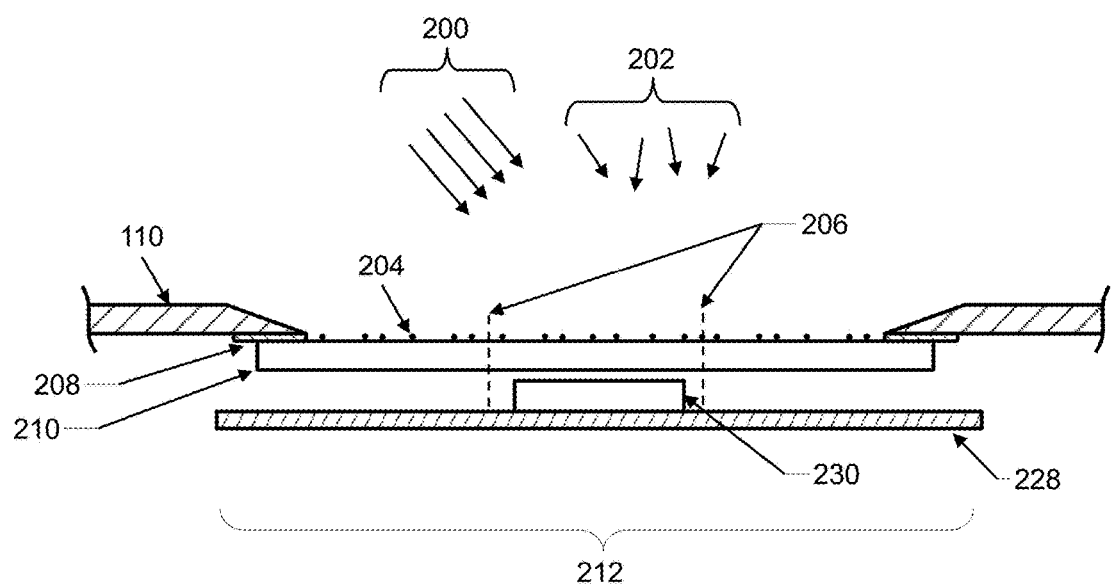
FIG. 5 depicts a cross-sectional view of another embodiment of a soiling sensor, wherein imaging optics are omitted.

FIG. 5 depicts an alternative, in accordance with some embodiments, in which imaging optics (216) are omitted, image sensor (230) is placed directly underneath transparent window (210), and soiling particles (204) are imaged by the shadows they cast directly onto image sensor (230).

Additional embodiments may include combinations of elements depicted in FIG. 3, FIG. 4, and/or FIG. 5.

In some embodiments, soiling sensor (108) may be heated to remove condensation of water droplets on transparent window (210) which could interfere with the soiling sensor (108).

In some embodiments, an optional irradiance sensor (106), comprising for example a PV reference cell, is joined to soiling sensor (108) as part of a system, either within enclosure (110) or in a separate enclosure.

Figure 6:
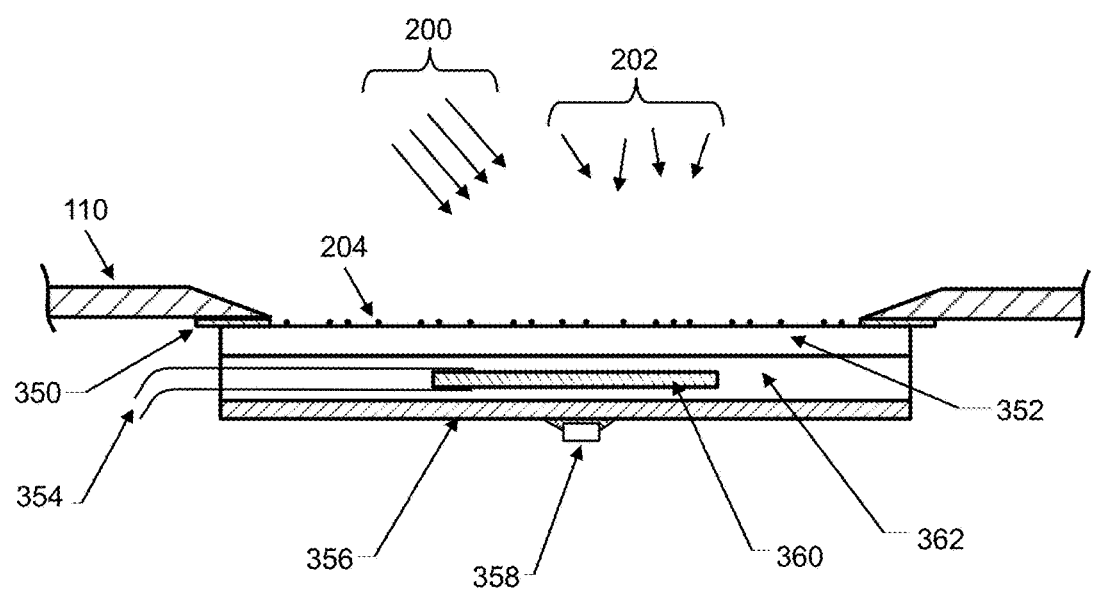
FIG. 6 depicts a cross-sectional view of an embodiment of an irradiance sensor comprising an encapsulated PV cell.

FIG. 6 depicts an irradiance sensor (106) in accordance with some embodiments. A PV cell (360) with electrical leads (354) is encapsulated between a transparent window (352), typically fabricated of glass, and a backsheet layer (356), using a transparent encapsulant material (362). This encapsulated PV cell (360) assembly may be bonded with a seal material (350) to enclosure (110) at a window opening cut in enclosure (110), allowing direct sunlight (200) and/or diffuse sunlight (202) to illuminate PV cell (360). A temperature sensor (358), such as a Resistive Temperature Device (RTD) measures PV cell (360) temperature. Measurement of PV cell (360) short-circuit current corrected for temperature variation using measurements from temperature sensor (358) are used to determine the irradiance incident on the irradiance sensor (106). In some embodiments encapsulated PV cell (360) assembly is bonded to the inside of enclosure (110), as depicted in FIG. 6, while in other embodiments it is bonded to the outside of enclosure (110), in order to avoid traps for the collection of soiling particles (204).

Alternative embodiments of irradiance sensor (106) include a photodiode or a thermopile pyranometer.

In some embodiments, irradiance sensor (106) may be used to determine optimal illumination conditions for acquiring images from image sensor (230) for operation of soiling sensor (108).

In some embodiments, readings from soiling sensor (108) may be used to correct readings of irradiance sensor (106) for the effects of soiling particles (204) accumulated on the surface of irradiance sensor (106), thereby improving the accuracy of irradiance sensor (106) and eliminating the need to clean it. In this embodiment both soiling and irradiance may be measured without maintenance for cleaning of either sensor.

In some embodiments, irradiance sensor (106) paired with soiling sensor (108) may be used to calibrate soiling sensor (108), by comparing readings from both irradiance sensor (106) and soiling sensor (108) before and after cleaning.

Figure 7:
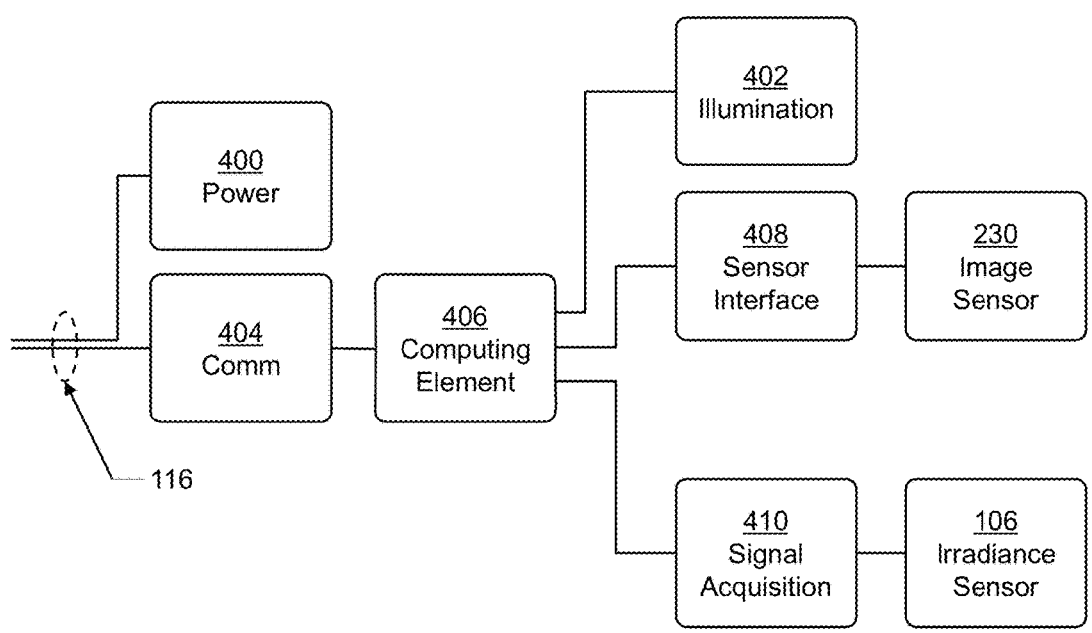
FIG. 7 depicts a block diagram of major functional electronic elements of an embodiment comprising a soiling sensor and irradiance sensor.

FIG. 7 depicts a block diagram of functional electronic elements in accordance with some embodiments. Power and communications cabling (116) may bring electric power and communication signals to the device, either in a single cable or multiple cables. Power circuitry (400) delivers electric power as needed to all other functional elements. Communication circuitry (404) may relay data and commands to and from computing element (406), which may control the device and perform measurement and data analysis. Computing element (406) may comprise a microcontroller or microprocessor (or another computing device) with typical features including volatile and non-volatile memory, program data, I/O, real-time clock, etc. Computing element (406) may communicate with image sensor (230) via a sensor interface (408) in order to control and record data from image sensor (230); acquire data from optional irradiance sensor (106) via signal acquisition electronics (410); and control optional illumination (402) which drives illumination sources (224).

In various embodiments functional elements depicted in FIG. 7 may be integrated together in a lesser or greater number of separate components and either entirely within enclosure (110) or utilizing additional enclosures.

In some embodiments, a single-board computer serves the functions of power circuitry (400), communication circuitry (404), computing element (406), sensor interface (408), and signal acquisition (410).

In some embodiments, communication of data and commands may be performed via communication circuitry (404) over Ethernet; in other embodiments, it may be performed via RS-485. In an exemplary embodiment, communication of data and commands uses an industrial communications protocol such as MODBUS.

In some embodiments, computing element (406) may perform measurement and data analysis and store and report results. In other embodiments, a remote computer or computing device may perform various levels of image processing, data analysis, and/or reporting to achieve final results.

The resolution and field of view (206) of the images acquired by soiling sensor (108) may be inter-related. With respect to an object plane comprised by the exterior surface of transparent window (210) with accumulated soiling particles (204), the resolution of images formed at image sensor (230) is the size of the smallest discernable feature in the object plane, and the field of view (206) is the size of the portion of the object plane that is viewable. The resolution and field of view (206) are determined by imaging optics (216), focal lengths, and the pixel size of image sensor (230). In general, achieving smaller resolution requires smaller field of view (206), for given imaging optics (216).

In some embodiments, resolution is chosen to be smaller than a characteristic size of soiling particles (204), so that soiling particles (204) may be individually discerned. Here a characteristic size means, for example, a diameter smaller than the diameter of substantially all or of a specified percentage, e.g. 66% or 90% or 95%, of soiling particles (204), or an average or median diameter of soiling particles (204). However, this limits field of view (206). For example, with a resolution of 1 micron and an exemplary image sensor having a 2592×1944 pixel array, field of view (206) is limited to approximately 2.5 mm. Larger field of view (206) may be desirable as the deposition of soiling particles (204) may not be uniform.

Therefore, in other embodiments, resolution is chosen to be larger than a characteristic size of soiling particles (204) (as discussed above) and only small enough to discern at least a portion of the clear spaces in between soiling particles (204). This results in a larger resolution parameter which permits a larger field of view (206). Maximizing field of view (206) in this way may be beneficial because the area density of deposited soiling particles (204) may be non-uniform, such that measurements from a small field of view (206) may be less accurate than measurements from a large field of view (206). For example, in various embodiments, field of view (206) may be chosen to be 5-10 mm or greater.

Determination of required resolution may depend on the size distribution of soiling particles (204). This size distribution may vary according to the type of soiling particles (204) found at a particular site. An exemplary size distribution of soiling particles (204) is provided by the international standard "ISO 12103-1, A2 Fine Test Dust" published by the International Organization for Standardization, which represents airborne particulate matter of the type that may accumulate as soiling particles (204) on PV arrays (100). Test dust complying with this standard comprises approximately 5% particles with diameter of 1 micron or less and approximately 2% with diameter of 100 microns or greater, with a median diameter of approximately 10 microns.

Figure 8:
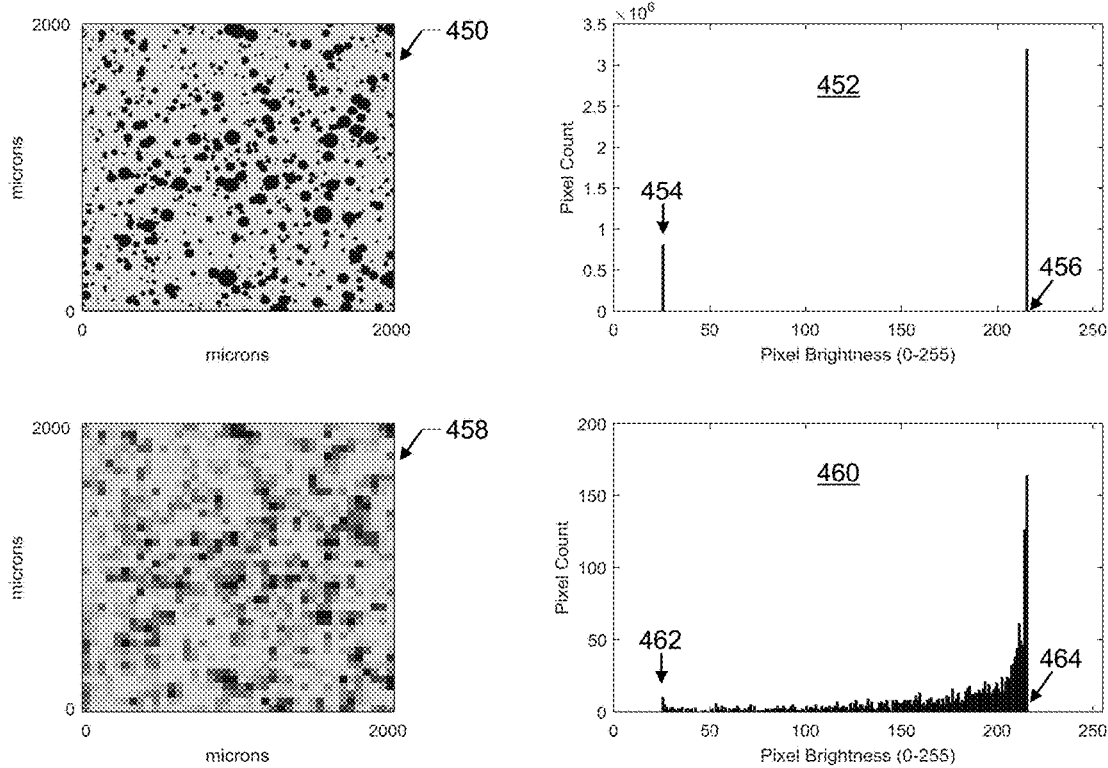
FIG. 8 depicts simulated images captured in two different resolutions together with their pixel brightness histograms.

FIG. 8 illustrates determination of the resolution parameter and aspects of image analysis in accordance with some embodiments. The figure depicts a simulated image (450) that could be acquired by a soiling sensor (108) with transparent window (210) illuminated by sunlight (200, 202). Simulated image (450) depicts a 2000 micron×2000 micron region of soiling particles (204) randomly selected with a size distribution according to ISO 12103-1 A2. Simulated image (450) is created with a resolution of 1 micron, so that even many of the smallest soiling particles (204) are discernable. Pixel brightness histogram (452) depicts the distribution of pixel brightness values, on a 0-255 scale, for simulated image (450). We denote the pixel brightness values corresponding to maximum (i.e. 100%) and minimum (i.e. 0%) relative transmission of sunlight (200, 202) $B_{transparent}$ and $B_{opaque}$, respectively. Note that $B_{opaque}$ may be a non-zero pixel brightness, due to scattered light that enters image sensor (230), dark current in image sensor (230), and other factors; also $B_{transparent}$ may be lower than 255 depending on the brightness of sunlight (200, 202) illuminating the transparent window (210), exposure time and sensitivity of image sensor (230), and other factors. Therefore, $B_{opaque}$ and $B_{transparent}$ must be determined in order to analyze the image. Clear spaces in simulated image (450) in between soiling particles (204) have pixel brightness values of 215 which is identified as $B_{transparent}$ (456) on pixel brightness histogram (452), while pixels within shadows of soiling particles (204) have pixel brightness value of 25 which is identified as $B_{opaque}$ (454). The average transmission of sunlight (200, 202) corresponding to simulated image (450), approximately 80%, is found by dividing the count of pixels at $B_{transparent}$ (456) by the sum of the counts of pixels at $B_{transparent}$ (456) and $B_{opaque}$ (454). Resampled simulated image (458) depicts the same image as simulated image (450) but with the 1 micron pixels of simulated image (450) aggregated into 50 micron pixels in resampled simulated image (458). The smallest soiling particles (204) are no longer individually discernable but instead contribute to a continuum of gray scale values. Pixel brightness histogram (460) corresponding to resampled simulated image (458) clearly displays $B_{transparent}$ (464) and $B_{opaque}$ (462) values equal to $B_{transparent}$ (456) and $B_{opaque}$ (454) of pixel brightness histogram (452), but also displays significant pixel counts for intermediate pixel brightness values corresponding to the range of gray values for pixels in resampled simulated image (458). The average transmission of sunlight (200, 202) corresponding to resampled simulated image (458) is calculated by taking the average over all analyzed pixels of $(B_i - B_{opaque})/(B_{transparent} - B_{opaque})$, where $B_i$, is the pixel brightness value of an individual pixel number i. This average is found to be approximately 80% as for simulated image (450). Therefore, although the smallest soiling particles (204) are not individually discernable with the resolution of 50 microns in resampled simulated image (458) and even though the resolution is larger than the average soiling particle (204) diameter, the average transmission of sunlight (200, 202) can still be determined. However, if the pixel size of resampled simulated image (458) were increased further, at a certain limit all pixels would consist of a mixture of regions with and without soiling particles (204) and the $B_{opaque}$ and $B_{transparent}$ values would no longer be discernable in the corresponding pixel brightness histogram which would consist primarily of intermediate gray values. In this case it would not be possible to determine average transmission of the image for lack of the reference values $B_{opaque}$ and $B_{transparent}$.

Simulations with soiling particle (204) size distribution according to ISO 12103-1 A2 show that image resolution up to approximately 50-100 micron may still allow sufficiently accurate identification of the $B_{transparent}$ value for soiling levels up to approximately 20%. In an exemplary embodiment, imaging optics (216) and magnification (based on focal positions) are selected so that each pixel of image sensor (230) corresponds to 5 micron on the object plane corresponding to the exterior surface of transparent window (210). With an exemplary image sensor using a 2592×1944 pixel array, this corresponds to a field of view (206) approximately 13 mm×10 mm. However, with typical imaging optics (216) the minimum resolution is dominated by the quality of imaging optics (216) as well as focal precision, rather than pixel size of image sensor (230), and may be approximately 20 microns. A smaller resolution can be achieved with higher quality imaging optics (216) or by limiting field of view (206). However, a resolution of 20 microns may be sufficient as discussed above.

In some embodiments, the value of $B_{transparent}$ is determined as the maximum pixel brightness value in an image to be analyzed. However, in some cases, the maximum pixel brightness value does not correspond accurately to the value of $B_{transparent}$ which should be the pixel brightness corresponding to regions of 100% transmission of sunlight (200, 202), because some pixels may have higher brightness value than $B_{transparent}$. This may occur, for example, due to variations in image sensor (230) sensitivity, spurious high-brightness pixels in image sensor (230), noise, image compression artifacts, reflections of light from edges of soiling particles (204) or parts of the device, and other factors. It is advantageous to suppress such sources of extra-bright pixels. However, since it may not be possible to completely suppress such sources, in some embodiments $B_{transparent}$ is determined as the pixel brightness value that is larger than that of a particular percentage of pixels. In an exemplary embodiment, the threshold is 98%. In other embodiments, $B_{transparent}$ is determined as the most common pixel brightness value, i.e. the mode of the distribution, since for sufficiently low soiling levels (for example, less than 20-50%), the most common pixel brightness value is associated with portions of the object plane which are free of soiling particles. In some embodiments, $B_{transparent}$ is determined as the most common pixel brightness value amongst a subset of pixels with higher than average brightness, i.e. the mode of the distribution of the pixels with brightness above a threshold value, where an exemplary value of the threshold may be 75% of full brightness.

In some embodiments, the value of $B_{opaque}$ is determined by identifying the minimum pixel brightness value, as depicted in FIG. 8 by $B_{opaque}$ (454) and $B_{opaque}$ (462). However, it is not always possible to determine the $B_{opaque}$ value in this manner. For example, if all soiling particles (204) observed in the image are smaller than the resolution, then each dark pixel is an average of clean and soiled regions of transparent window (210) and the minimum pixel brightness is no longer equal to the $B_{opaque}$ value, which should be the pixel brightness corresponding to 0% transmission through the corresponding region of the transparent window (210). Furthermore, for images corresponding to a completely clean or almost completely clean transparent window (210), i.e. a situation with average transmission of sunlight (200, 202) near 100%, there may not be any pixel with brightness near the value of $B_{opaque}$. Therefore, in some embodiments, $B_{opaque}$ is determined instead as a fixed ratio of $B_{transparent}$, wherein said ratio is determined during a design or calibration step, using for example intentional soiling of transparent window (210), and is stored in non-volatile memory. In other embodiments, the value of $B_{opaque}$ is ensured to be approximately 0, by limiting the exposure time of image sensor (230) and limiting stray light, for example using a shroud (252) as depicted in FIG. 4 and/or keeping interior surfaces of the soiling sensor (108) black and unreflective where possible.

Figure 9:
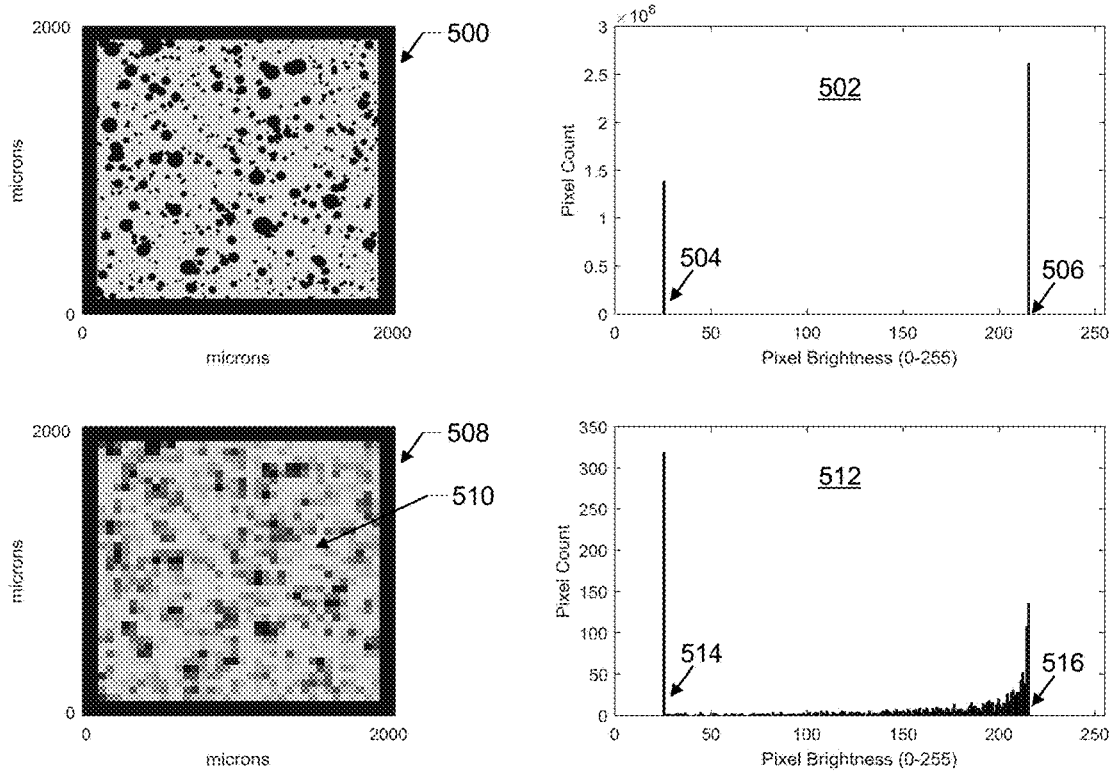
FIG. 9 depicts simulated images captured in two different resolutions, for an embodiment comprising an aperture, together with their pixel brightness histograms.

In other embodiments, an aperture (250) blocking a portion of field of view (206), as depicted in FIG. 4, provides a reference for determination of $B_{opaque}$, especially in conditions of low soiling or soiling without large soiling particles (204). Pixels within the image obscured by aperture (250) correspond to 0% light transmission and can therefore be used to reliably determine the $B_{opaque}$ value. FIG. 9 depicts an analysis of simulated images in such an embodiment. Simulated image (500) of a 2000 micron×2000 micron region of the object plane is created with 1 micron pixel size so that the smallest soiling particles (204) are discernable. The thick black region around the perimeter of simulated image (500) corresponds to a shadow of aperture (250), which in an actual image might appear slightly blurred and out of focus. Pixel brightness histogram (502) corresponding to simulated image (500) displays peaks at $B_{opaque}$ (504) and $B_{transparent}$ (506) but no other peaks, since all pixels are either light gray or black. Resampled simulated image (508), which is the same as simulated image (500) but with 50 micron pixels, displays pixels with a range of gray values. Its corresponding pixel brightness histogram (512) displays a peak at $B_{transparent}$ (516) and includes a very prominent peak at $B_{opaque}$ (514)—in contrast to the weak peak at $B_{opaque}$ (462)—due to the inclusion of dark pixels corresponding to the shadow of aperture (250). Thereby the value of $B_{opaque}$ (514) is easily determined. However, once $B_{opaque}$ (514) is determined, to determine the average transmission of sunlight (200, 202) corresponding to resampled simulated image (508), only the region (510) not blocked by aperture (250) is used in calculation, to remove from analysis pixels in the shadow of aperture (250).

Figure 10:
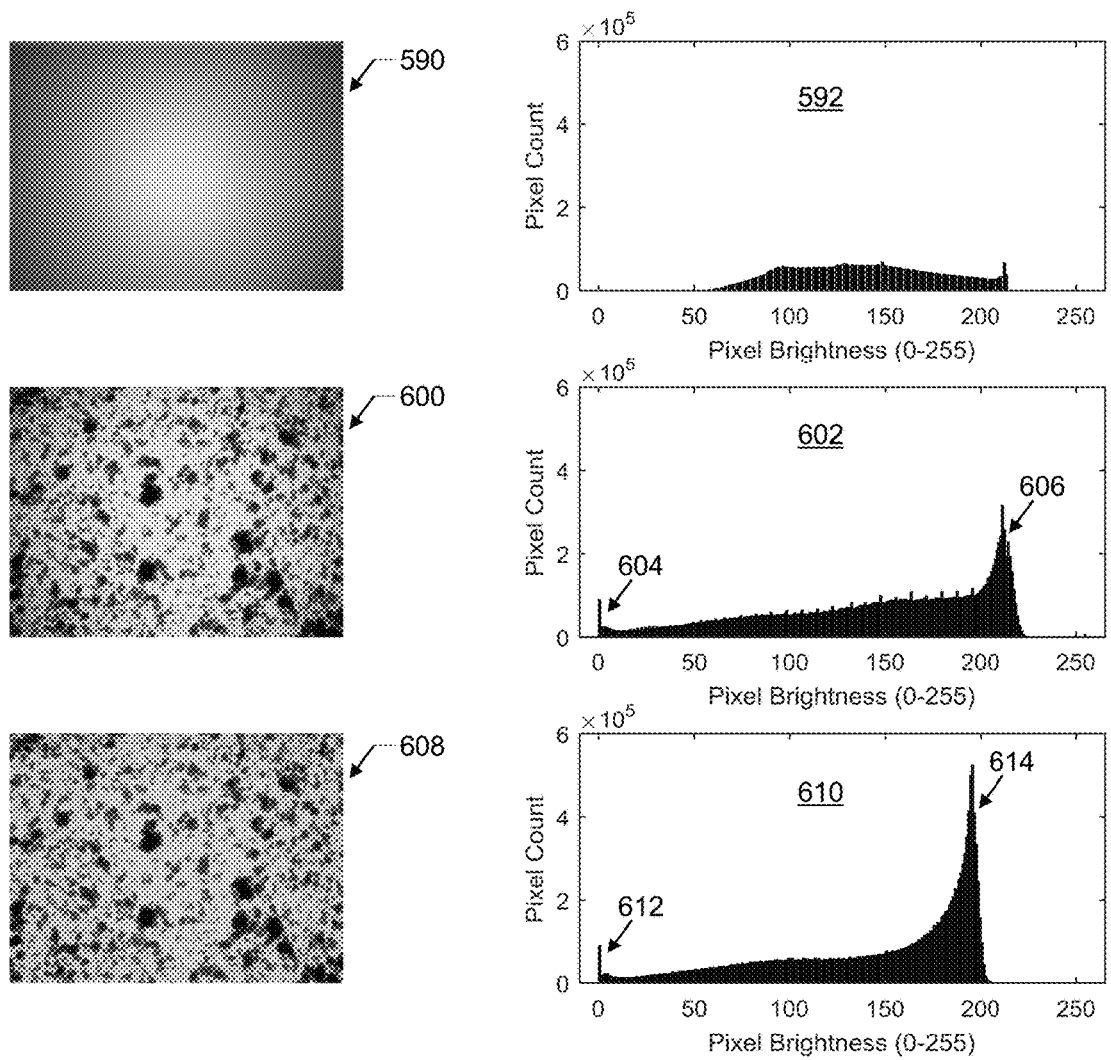
FIG. 10 depicts an exemplary image of soiling particles on a transparent window together with a corrected image, and the pixel brightness histograms of the original image and corrected image.

FIG. 10 depicts real images from an exemplary embodiment of soiling sensor (108), displaying additional features not found in the simulated images depicted in FIG. 8 and FIG. 9. Image (590) was taken with transparent window (210) completely clean. Although no soiling particles (204) are present, image (590) nevertheless does not have uniform pixel brightness, but instead has a range of pixel brightness values, varying from center to edge, as seen in its corresponding pixel brightness histogram (592). Such variation can be caused by spatially varying optical throughput of imaging optics (216), varying sensitivity of image sensor (230), and other factors. Image (590) can be regarded as a background (or baseline) image for soiling sensor (108). Image (600) was taken with the same exemplary embodiment of soiling sensor (108) but with a sample of ISO 12103-1 A2 soiling particles (204) applied to transparent window (210). Minimum (604) and maximum (606) pixel intensity values are evident in its corresponding pixel brightness histogram (602). However, image (600) displays pixel brightness variations due to background variation, as in image (590), which are not associated with soiling particles (204).

Therefore, in some embodiments, before image (600) is analyzed to determine average transmission of sunlight (200, 202) it is corrected for the effects of non-uniform background. In some embodiments, a background image is determined. In some embodiments, said background image is taken as a baseline image, such as image (590), acquired when soiling sensor (108) is initially calibrated or otherwise known to be clean. In other embodiments, said background image is determined as an initial step in analysis of images acquired by soiling sensor (108). using Fourier filtering, fitting of a function (for example a polynomial) to the image, using the rolling ball background determination algorithm ("Biomedical Image Processing", Stanley Sternberg, IEEE Computer, January 1983), or other background subtraction techniques, including techniques described below. In some embodiments, correction of images is performed by dividing each pixel of an acquired image, such as acquired image (600), by its corresponding pixel in the background image, such as image (590). In other embodiments, the correction is performed by subtracting the background, rather than dividing by it.

Image (608) depicts the same image as (600) after background correction. The clear spaces in image (608) between soiling particles (204) are of uniform brightness, and corresponding pixel brightness histogram (610) of image (608) has a sharp peak near $B_{transparent}$ value (614). A $B_{opaque}$ (612) value of 0 is also evident. Background-corrected image (608) can be analyzed to determine average transmission of sunlight (200, 202) by assigning to each pixel a fractional transmission value between $B_{opaque}$ and $B_{transparent}$ and averaging the fractional transmission values of all pixels, as described above.

In some embodiments, background correction may be performed according to the following steps: an acquired image is subdivided into regions, for example approximately 100×100 pixels in the case of an exemplary image sensor having 2592×1944 pixels; each region is analyzed to determine its most common pixel brightness value, or its most common pixel brightness value from amongst its brightest pixels, as discussed above, and this value is assigned as the value of $B_{transparent}$ corresponding to said region; and the pixel brightness values of each of said regions are divided by their corresponding $B_{transparent}$ value, or the corresponding $B_{transparent}$ value is subtracted from said pixel brightness values.

Figure 11:
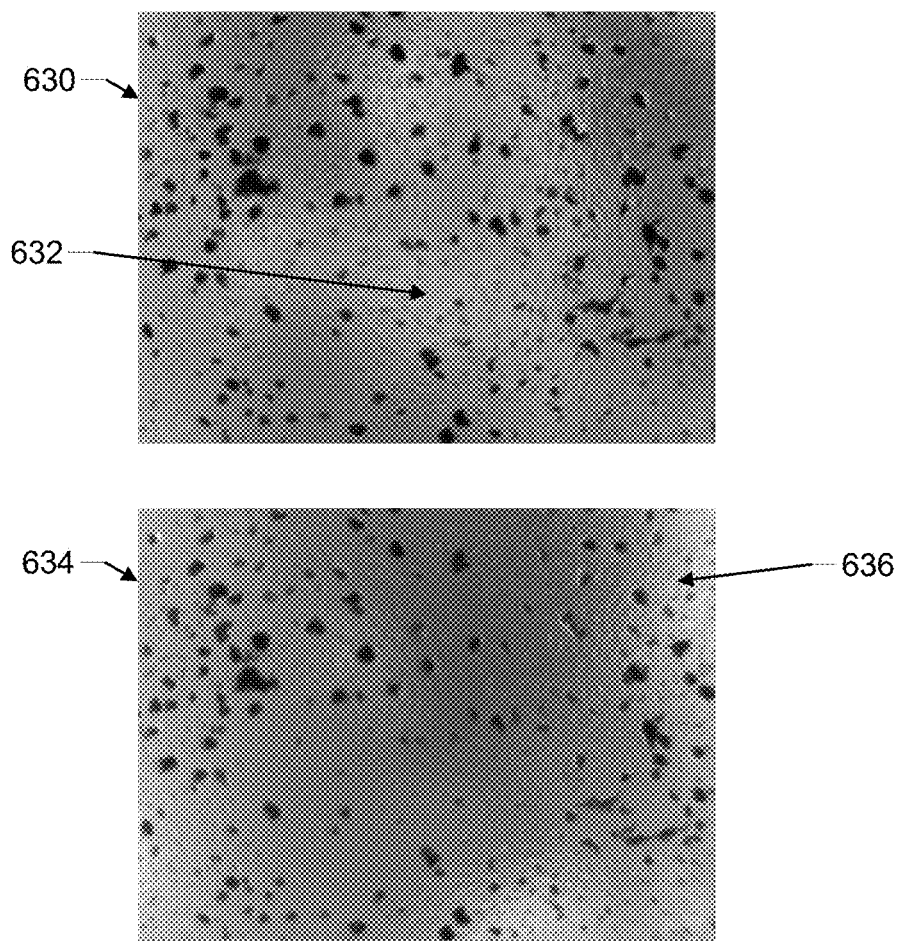
FIG. 11 depicts exemplary images of soiling particles on a transparent window showing clouds in the background.

Although imaging optics (216) are focused on the object plane comprising the exterior surface of transparent window (210), objects in the sky above soiling sensor (108), such as clouds, birds, or aircraft, may still appear in images captured by image sensor (230), although out of focus. FIG. 11 depicts two images captured minutes apart by an exemplary embodiment of soiling sensor (108). Image (630) and image (634) show cloud (632) and cloud (636) above soiling particles (204). Cloud (632) and cloud (636) would cause variations in pixel brightness not associated with soiling particles (204) and therefore measurement error. Therefore, in some embodiments, the effect of clouds (632, 636) and other moving objects in the sky is removed prior to image analysis. In some embodiments, the effect of clouds and other moving objects in the sky is removed by averaging a sequence of images acquired from image sensor (230) over a period of time, causing clouds and other moving objects in the sky to disappear. In some embodiments, after averaging a number of images to obtain an averaged image, the averaged image is further corrected by applying background correction as discussed above. In other embodiments, background correction as discussed above is performed on each acquired image prior to averaging images together.

The characteristics and quality of images acquired at image sensor (230) depend upon the lighting conditions of soiling particles (204) and transparent window (210).

Figure 12:
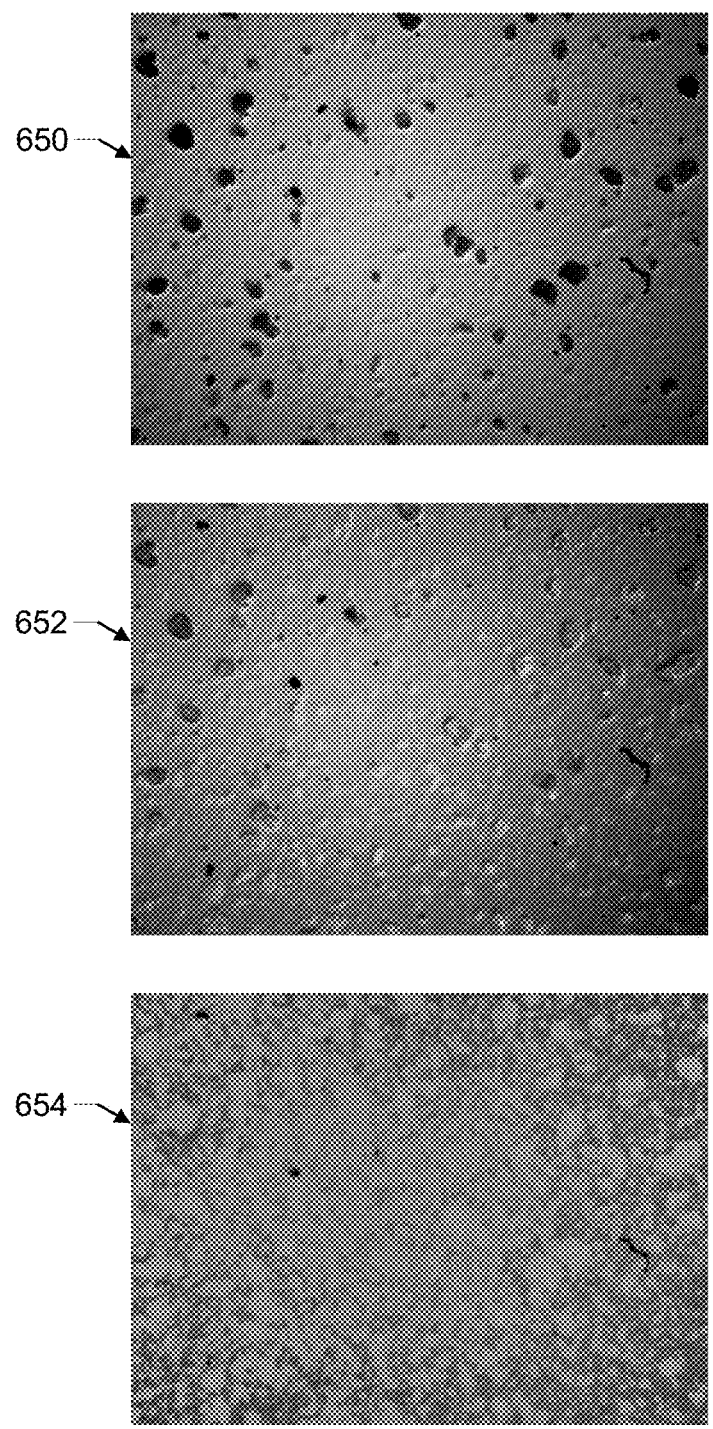
FIG. 12 depicts exemplary images of soiling particles on a transparent window with varying amounts of direct sunlight versus diffuse sunlight.

FIG. 12 depicts three images of soiling particles (204) illuminated by direct sunlight (200) and/or diffuse sunlight (202) acquired by image sensor (230) in an embodiment similar to that depicted in FIG. 3, under completely clear sky conditions. Image (650) was acquired during morning twilight approximately at sunrise; the illumination is therefore predominantly from diffuse sunlight (202) with very little contribution from direct sunlight (200). Shadows of soiling particles (204) are very clear in image (650), although image (650) also shows some bright outlines around larger soiling particles (204) arising from reflection of direct sunlight (200) from the sides of soiling particles (204). These reflections are undesirable since they contribute to pixel intensities higher than $B_{transparent}$. Image (652), of the same sample of soiling particles (204), was acquired later in the morning and includes a higher contribution of direct sunlight (200); reflection of direct sunlight (200) now obscures more of the soiling particles (204). Image (654), of the same sample, was acquired close to noon with direct sunlight (200) striking transparent window (210) at a low angle of incidence. In this case reflection of direct sunlight (200) inside enclosure (110) and/or between the interior and exterior surfaces of transparent window (210) causes the soiling particles (204) to be illuminated significantly from below, so that they appear as white spots rather than dark shadows.

In some embodiments, to simplify image analysis, acquisition or analysis of images may be performed only (or preferentially) for conditions of predominantly diffuse sunlight (202) illuminating transparent window (210), with minimal contribution from direct sunlight (200). In some embodiments, predominantly diffuse sunlight (202) conditions may be selected by using images acquired only (or preferentially) during times near sunrise or sunset, including morning twilight or evening twilight. In some embodiments, times of sunrise, sunset, morning twilight, and/or evening twilight may be determined by computing element (406) with reference to a real-time clock and optionally by taking into account the latitude and longitude of the installation site. In other embodiments, predominantly diffuse sunlight conditions are selected based on a threshold value for irradiance measured by irradiance sensor (106), or by image sensor (230), or by another irradiance measurement device, where such conditions may occur at morning or evening, or also during periods of cloud cover, or also for other conditions that block direct sunlight (200).

In some embodiments, to remove the effects of reflections from the sides of soiling particles (204) such as observed in image (650), images are processed with a deconvolution algorithm.

Figure 13:
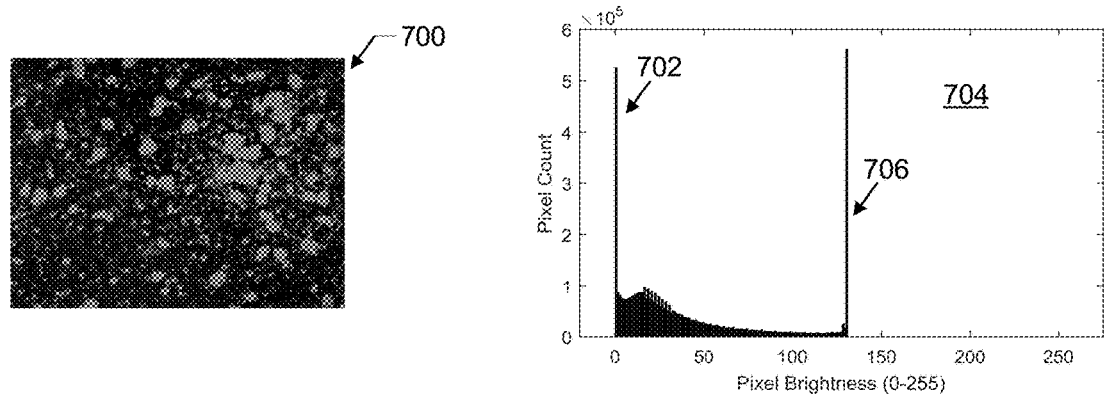
FIG. 13 depicts an exemplary image of soiling particles on a transparent window illuminated by light emanating from within an enclosure, for example at night, together with its corresponding pixel brightness histogram.

In some embodiments, soiling particles (204) on transparent window (210) may be illuminated from underneath by light generated inside sealed enclosure (110), for example at night, by illumination sources (224). FIG. 13 depicts an exemplary image (700) acquired in such an embodiment, acquired at night. In this embodiment, bright pixels correspond to reflection from soiling particles (204) while dark pixels correspond to clear spaces between the soiling particles (204). Accordingly bright pixels are assigned low values of external light transmission and dark pixels are assigned high values of external light transmission. Therefore in pixel brightness histogram (704) corresponding to image (700) the value of $B_{transparent}$ (706) is 0 while the value of $B_{opaque}$ (702) is 130.

In some embodiments, images corresponding to illumination of soiling particles (204) from underneath are analyzed by determining a value $B_{opaque}$, corresponding to 0% transmission of sunlight (200, 202), from the brightest pixels; determining a value $B_{transparent}$, corresponding to 100% transmission of sunlight (200, 202), from the darkest pixels; assigning each pixel a fractional transmission value between 0% and 100% according to its relative brightness between $B_{opaque}$ and $B_{transparent}$; and averaging the fractional transmission values of all pixels. In other embodiments, such images may be analyzed by first inverting the image, so that soiling particles (204) appear dark and the clear spaces between them appear light, determining $B_{opaque}$ and $B_{transparent}$ respectively from the darkest and brightest pixels, and calculating the fractional transmission of each pixel and the average of all transmission values.

In some embodiments, illumination of soiling particles (204) from underneath is performed only at night. In other embodiments, illumination of soiling particles (204) from underneath is performed during the day and/or night, with illumination sources (224) producing bright enough light to overcome the effect of sunlight (200, 202). In some embodiments, illumination sources (224) may be operated in a pulsed high brightness mode similar to a flash camera.

In some embodiments, illumination of soiling particles (204) from underneath may be performed without illumination sources (224) by relying on the natural reflection of direct sunlight (200) and/or indirect sunlight (202) within enclosure (110) and/or between the surfaces of transparent window (210), as depicted in image (654).

In some embodiments, analysis results achieved with illumination of soiling particles (204) from above vs. from underneath may be compared and an average or highest-confidence result may be used. For example, in conditions of very high soiling when clear spaces in between soiling particles (204) are small, illumination from underneath soiling particles (204) may yield more accurate results than illumination from above soiling particles (204). In some embodiments, comparison of analysis results achieved with illumination of soiling particles (204) from above vs. from underneath is used to detect error conditions, such as fouling of soiling sensor (108) by debris or bird droppings. For example, a condition in which soiling sensor (108) is covered by bird droppings could result in images utilizing illumination by sunlight (200, 202) appearing of uniform brightness, without shadows from soiling particles (204), while images utilizing illumination by illumination sources (224) would be very bright due to reflection from the bird droppings, indicating that transparent window (210) is no longer clean, and the error condition could be detected.

In some embodiments, as depicted in FIG. 5, imaging optics (216) may be omitted and image sensor (230) may be placed directly underneath transparent window (210), which may be fabricated from a filter glass material to reduce light intensity, and soiling particles (204) are imaged by the shadows they cast directly onto image sensor (230). Here directly underneath means as close as possible or even in direct contact, to minimize spreading of shadows cast by soiling particles (204). In such embodiments, image resolution may be determined by the angular distribution of the illumination rays and the geometric expansion of shadows as they propagate to image sensor (230), in addition to the pixel size of image sensor (230). These embodiments may have improved performance in direct sunlight (200) (which is nearly collimated) and reduced performance in diffuse sunlight (202) (which includes a broad range of angular distribution of light rays) relative to embodiments such as in FIG. 3 and FIG. 4.

Figure 14:
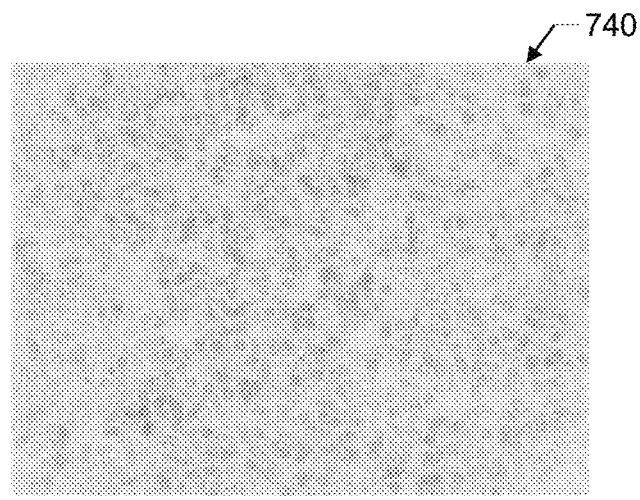
FIG. 14 depicts an exemplary image of soiling particles on a transparent window in an embodiment without imaging optics as depicted in FIG. 5.

FIG. 14 depicts an exemplary image (740) of light-colored, partially transparent soiling particles (204) on transparent window (210) acquired with an embodiment without imaging optics (216) such as depicted in FIG. 5.

In some embodiments, enclosure (110) may comprise at least two soiling sensors (108), wherein at least one soiling sensor (108) includes imaging optics (216), for example as depicted in FIG. 3 or FIG. 4, and at least one does not include imaging optics (216) but has image sensor (230) directly underneath transparent window (210), for example as depicted in FIG. 5, and soiling level is determined from measurements of both kinds of soiling sensors (108) or from whichever kind of soiling sensor (108) is most appropriate for given lighting conditions. For example, in this embodiment, one soiling sensor (108) may be used with predominantly direct sunlight (200) while another would be used with predominantly diffuse sunlight (202) and illumination from illumination sources (224).

In some embodiments, enclosure (110) may comprise two or more soiling sensors (108) of one or both types discussed above, wherein multiple soiling sensors (108) provide for measurement redundancy or accuracy improvement through collection of additional data.

Image sensor (230) and PV array (100) may each respond differently to the spectral distribution of incident direct sunlight (200) and/or diffuse sunlight (202). Therefore, in some embodiments, the average transmission determined from analysis of images captured by image sensor (230) may be corrected by a spectral correction factor so that it more closely approximates the true soiling ratio of PV array (100). In some embodiments, the spectral correction factor may be based on a model of the wavelength-dependent light transmission through soiling particles (204), the wavelength-dependent response of image sensor (230), the wavelength-dependent response of the PV technology used in PV array (100), and the measured or assumed spectral distribution of incident direct sunlight (200) and/or diffuse sunlight (202). In some embodiments, said correction factor may be determined using a method analogous to the spectral mismatch factor correction applied to calibrating photovoltaic devices (K. A. Emery, et al, *IEEE PV Specialists Conference*, pp. 623-628, 1985). In other embodiments, said correction factor may be determined through empirical calibration in comparison to a specific or generic PV technology.

In some embodiments, image sensor (230) is insensitive to color and produces a monochrome gray-scale output.

In other embodiments, image sensor (230) may be sensitive to color. Exemplary image sensors (230) may include a color filter in which individual pixels are filtered to respond to either red, green, or blue light. In some embodiments, interpolation between pixels of each filter color produce a separate approximated image for each color channel. In some embodiments, images acquired from each color channel are analyzed individually as described above, and overall results for average transmission are reported as an average or in some embodiments as a weighted average of the results for the different color channels. In some embodiments, analysis of color data from image sensor (230) may be used to estimate the overall loss in photovoltaic device output over a wide wavelength range, including potentially wavelengths outside the range of sensitivity of image sensor (230), by employing a model of the wavelength-dependent light transmission of soiling particles (204) coupled with the wavelength-dependent response of PV array (100). In some embodiments, color data may be used to classify soiling particles (204) as among a type that transmit more light in the near-infrared region of the spectrum than in the visible and UV regions, or vice versa, even though near-infrared and UV wavelength ranges may, in some embodiments, be outside the range of sensitivity of image sensor (230). In some embodiments, classification of soiling particles (204) may be used to estimate wavelength-dependent properties of soiling particles (204) and thereby calculate a spectral correction factor for the average transmission determined through analysis of images from image sensor (230).

In some embodiments, color data from image sensor (230) may be used to identify clear areas in between soiling particles (204) in order to better determine the pixel brightness value $B_{transparent}$ corresponding to areas of 100% transmission. For example, clear areas in between soiling particles (204) may have more blue light due to imaging the sky.

In some embodiments, stored calibration values may be used to correct images from image sensor (230) or the measurements of average transmission determined from the images. In some embodiments, a spectral correction factor is used. In other embodiments, corrections are performed to minimize various imperfections, including, for example, scratches or other marks on transparent window (210), non-linearity of image sensor (230), non-uniformity of image sensor (230), and other artifacts.

Figure 15:
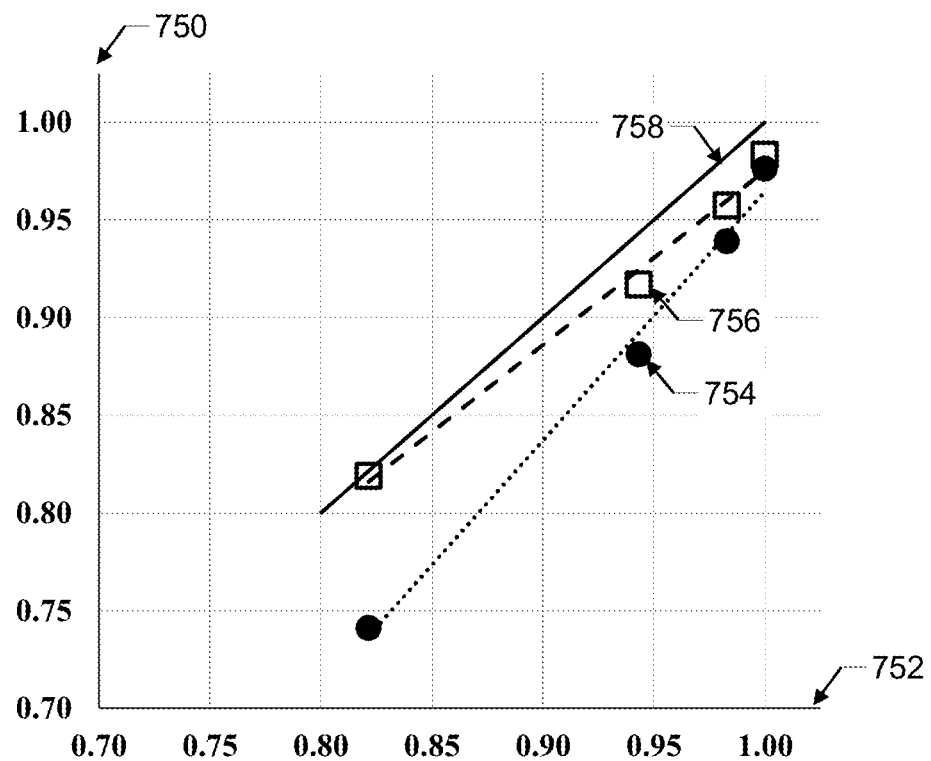
FIG. 15 depicts a correlation between average light transmission measured by an embodiment, plotted against vertical axis, and average light transmission of the same samples measured by a reference method, plotted against horizontal axis, showing both with calibrated data points and uncalibrated data points.

In some embodiments, average transmission determined from analysis of images from image sensor (230) may be calibrated by comparison to soiling ratio measurements of a PV cell or PV array. FIG. 15 depicts an example of such a calibration. For four distinct soiling conditions, average light transmission was determined from analysis of images from image sensor (230) according to the methods disclosed above and for the same soiling conditions soiling ratio was determined separately on a PV cell representative of PV array (100). Soiling ratio values determined from the PV cell are shown on the horizontal axis (752) and average transmission values from image analysis are shown on the vertical axis (750). Uncalibrated data points (754) show that average transmission determined from the image analysis was, in this example, somewhat lower than the soiling ratio of the PV cell, in comparison to an ideal correlation (758). Accordingly, a calibration factor can be applied to yield the calibrated data points (756) which are closer to ideal correlation (758). In other examples, calibration may or may not performed.

In some embodiments, analysis of images from image sensor (230) of soiling sensor (108) to determine a soiling level characteristic of PV array (100) may comprise a number of the following steps: determine if images should be acquired at any particular instance, by reference to a clock such as in computing element (406) and/or based on the current irradiance measured by irradiance sensor (106); acquire one or more images from image sensor (230) over a period of time; average the acquired images into a single image; normalize the image to account for non-uniformities or defects in imaging optics (216) and/or image sensor (230) and/or transparent window (210), for example by utilizing a stored baseline image corresponding to the clean state of soiling sensor (106); normalize the image a second time to account for residual background variation, for example using a background removal or fitting algorithm; smooth the image to reduce or eliminate spurious pixels, for example using a Gaussian blur algorithm; determine the pixel brightness values of the image corresponding to $B_{transparent}$ (100% light transmission) and $B_{opaque}$ (0% light transmission) according to methods disclosed above; calculate the transmission at each pixel based on its pixel brightness value between the limits $B_{opaque}$ and $B_{transparent}$ according to methods disclosed above; calculate the average transmission for all or substantially all pixels within the portion of the image to be analyzed, for one or more color channels; correct the average transmission by a spectral correction factor and/or additional correction factors, and/or combine the average transmission values of each color channel using an average or weighted average, in order to yield a value representative of the soiling ratio (equivalently, average transmission relative to the clean state, soiling level, etc.) of PV array (100). In alternative embodiments, the order of the foregoing steps may be changed and/or any of the steps may be omitted or supplemented by additional steps.

In some embodiments, analysis of images from image sensor (230) of soiling sensor (108) to determine soiling level characteristic of PV array (100) is performed using a neural network. For example, a convolutional neural network may be trained with a library of images corresponding to known soiling level to process images and yield a regression output of soiling level that best matches the training data. In some embodiments, the neural network analysis may be performed by computing element (406).

In some embodiments, analysis of images from image sensor (230) of soiling sensor (108) may exclude pixels affected by defects such as dust on the interior surface of transparent window (210) or on imaging optics (216), scratches on the interior and/or exterior surfaces of transparent window (210), defective pixels in image sensor (230), defective transmission of image data from image sensor (230), etc. In some embodiments, a pre-defined list of pixels of image sensor (230) may be excluded from analysis. In some embodiments, defective pixels and/or defective images may be automatically identified.

Although this disclosure is directed to the application of measuring soiling of photovoltaic arrays, it will be understood by those skilled in the art that the disclosed subject matter has other applications, including detection of soiling and fouling of glass and other optics in other areas of commerce and industry, and these additional applications are intended to be within the scope of this disclosure.

The invention claimed is:

1. A device comprising
   a transparent window,
   an imaging unit, and
   a computing element coupled to said imaging unit,
   wherein
   said device is configured to allow soiling particles to accumulate on a surface of said transparent window,
   said imaging unit is configured to capture an image of said surface, and
   said computing element is configured to perform analysis of said image to determine a soiling level of said transparent window,
   wherein said analysis comprises
   determining a reference brightness of said image corresponding to a clean state of said transparent window, and
   determining said soiling level based at least upon a brightness of said image relative to said reference brightness.

2. The device of claim 1, wherein said device is configured to analyze said image when captured with illumination provided by predominantly diffuse sunlight.

3. The device of claim 1, comprising internal illumination sources for said capturing of said image.

4. The device of claim 1, wherein said imaging unit comprises an image sensor directly beneath said transparent window.

5. The device of claim 1, wherein a resolution of said image is larger than a characteristic size of said soiling particles.

6. The device of claim 1, wherein said analysis comprises identifying pixels within said image corresponding to regions of said transparent window that are substantially free of said soiling particles, and wherein from said pixels said analysis determines said reference brightness.

7. The device of claim 1, wherein said image is corrected by normalizing it against a baseline image acquired when said transparent window is clean, or wherein said image is corrected by extracting from said image a background image and normalizing said image against said background image.

8. The device of claim 1, wherein said image comprises an average of multiple images acquired over a period of time.

9. The device of claim 1, wherein said analysis comprises
   determining said reference brightness as a pixel brightness value of said image $B_{transparent}$,
   determining a pixel brightness value $B_{opaque}$ of said image corresponding to substantially complete attenuation of light,
   assigning to each of a plurality of pixels of said image a relative brightness value between $B_{transparent}$ and $B_{opaque}$, and
   averaging said relative brightness values to determine a relative transmission of light corresponding to said image.

10. The device of claim 1, wherein said image includes two or more color channels, and wherein said analysis further comprises using said color channels together with a wavelength-dependent model of light transmission and/or reflection of said soiling particles.

11. The device of claim 1, further comprising an irradiance sensor upon which soiling particles accumulate, and wherein a reading of said irradiance sensor is corrected by said determination of said soiling level to account for soiling particles obscuring said irradiance sensor.

12. A method comprising
   capturing or receiving an image of soiling particles accumulating on a surface of a transparent window, and
   analyzing said image to determine a soiling level of said transparent window,
   wherein said analyzing comprises
   determining a reference brightness of said image corresponding to a clean state of said transparent window, and
   determining said soiling level based at least upon a brightness of said image relative to said reference brightness.

13. The method of claim 12, wherein said analyzing comprises identifying pixels within said image corresponding to regions of said transparent window that are substantially free of said soiling particles, and wherein from said pixels said analysis determines said reference brightness.

14. The method of claim 12,
   wherein said analyzing comprises
   determining said reference brightness as a pixel brightness value of said image $B_{transparent}$,
   determining a pixel brightness value $B_{opaque}$ of said image corresponding to substantially complete attenuation of light,
   assigning to each of a plurality of pixels of said image a relative brightness value between $B_{transparent}$ and $B_{opaque}$, and
   averaging said relative brightness values to determine a relative transmission of light corresponding to said image.

15. The method of claim 12, further comprising illuminating said transparent window with predominantly diffuse sunlight for said capturing of said image.

16. At least one non-transitory, machine-accessible storage medium having instructions stored thereon, wherein the instructions are configured, when executed on a machine, to cause the machine to perform operations comprising
   capturing or receiving an image of soiling particles accumulating on a surface of a transparent window, and
   analyzing said image to determine a soiling level of said transparent window, wherein said analyzing comprises
   determining a reference brightness of said image corresponding to a clean state of said transparent window, and
   determining said soiling level based at least upon a brightness of said image relative to said reference brightness.

17. The machine-accessible storage medium of claim 16, wherein said analyzing comprises identifying pixels within said image corresponding to regions of said transparent window that are substantially free of said soiling particles, and wherein from said pixels said analysis determines said reference brightness.

18. The machine-accessible storage medium of claim 16, wherein said analyzing comprises
   determining said reference brightness as a pixel brightness value of said image $B_{transparent}$,
   determining a pixel brightness value $B_{opaque}$ of said image corresponding to substantially complete attenuation of light,
   assigning to each of a plurality of pixels of said image a relative brightness value between $B_{transparent}$ and $B_{opaque}$, and averaging said relative brightness values to determine a relative transmission of light corresponding to said image.

\* \* \* \* \*